US 6,645,475 B2

(12) United States Patent
Franklin et al.

(10) Patent No.: US 6,645,475 B2
(45) Date of Patent: Nov. 11, 2003

(54) ANTIPERSPIRANT FORMULATIONS

(75) Inventors: Kevin Ronald Franklin, Bebington (GB); Daniel Albert Martindale, Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 196 days.

(21) Appl. No.: 10/192,141

(22) Filed: Jul. 10, 2002

(65) Prior Publication Data

US 2003/0086884 A1 May 8, 2003

(30) Foreign Application Priority Data

Jul. 11, 2001 (GB) ............................................. 0116945

(51) Int. Cl.[7] ............................. A61K 7/32; A61K 7/34; A61K 7/38; A61K 7/00
(52) U.S. Cl. .............................. 424/65; 424/66; 424/68; 424/400; 424/401
(58) Field of Search ............................. 424/65, 66, 68, 424/400, 401

(56) References Cited

U.S. PATENT DOCUMENTS

| 5,384,117 A | 1/1995 | Vu et al. ....................... 424/66 |
| 5,972,319 A | 10/1999 | Linn et al. ..................... 424/65 |

FOREIGN PATENT DOCUMENTS

GB 2 291 805 2/1996

*Primary Examiner*—Shelley A. Dodson
(74) *Attorney, Agent, or Firm*—Kevin J. Stein

(57) ABSTRACT

The invention anhydrous antiperspirant cream composition which comprises:

a) a particulate aluminum/zirconium astringent salt in an amount of from 5 to 30% by weight;

b) a wax in an amount of from 4 to 20% by weight, said wax comprising an aliphatic ester or monohydric alcohol wax; and c) a water-immiscible carrier having a refractive index that is less than 0.1 below the refractive index of the aluminum/zirconium astringent salt and comprising an aromatic ester having a melting point of below 25° C. and/or a non-volatile silicone oil having a refractive index of at least 1.5 in an amount of from 45 to 80% by weight, has excellent avoidance of visible deposits on topical application, both initially and also after leave-on, i.e. after prolonged atmospheric exposure.

12 Claims, No Drawings

ANTIPERSPIRANT FORMULATIONS

The present invention relates to antiperspirant formulations and in particular to anhydrous soft solid formulations.

BACKGROUND AND PRIOR ART

Humans perspire over much of the body, but there are some areas where perspiration is more intense or noticeable after a period of time, such as in the underarm, possibly on account of molecular transformations of excretions from the apocrine, endocrine or sebaceous glands. Antiperspirant formulations are commonly accepted in many societies as a means to obviate or prevent wet patches on human skin or on clothing in contact with the skin. Their application can also reduce body odour generation. The underarm (axilla) is one area where antiperspirant formulations are normally applied.

Antiperspirant formulations are available for application via several different types of dispenser. These include non-contact dispensers such as aerosols or squeeze spray dispensers or contact dispensers such a roll-on or cream or firm stick dispenser. The formulations dispensed include both hydrous or anhydrous compositions. One class of formulation which is favoured by various consumers in some parts of the world comprises anhydrous creams, sometimes called soft solids, in which a particulate antiperspirant active material, commonly an aluminum or aluminum/zirconium astringent salt or complex, is suspended in a water-immiscible carrier fluid which is structured by incorporation of sufficient structurant to enable the formulation to be dispensed under mild pressure through one or more apertures in the dispensing head of a container and remain in place on the dispensing head until applied to the skin, eg to the axilla.

Anhydrous creams can incorporate a range of antiperspirant active salts, but it is often considered advantageous to employ salts containing both aluminum and zirconium, on account of their measured effectiveness at controlling perspiration when topically applied to human skin. Such creams conveniently employ a wax or mixture of waxes to impart structure to the carrier fluid, in part at least because such structurants are readily available and cost effective. The carrier fluid in commercially available anhydrous cream products normally comprises a volatile silicone oil such as a volatile linear or cyclomethicone, by virtue of the desirable overall combination of properties of such materials.

However, one of the problems that can be present in anhydrous creams which are applied topically to human skin is the observation of visible white deposits, not only on the skin, but also when the formulation is transferred onto clothing. Transfer can arise by direct contact or by fractions of the applied formulation being dislodged from the skin surface, for example by brushing, and falling under the influence of gravity onto clothing that is directly underneath. These white marks can be found on clothing adjacent to armpits or in the region of the hips. Such marks are significantly disliked by consumers, who find them relatively difficult to remove except by washing. Washing is usually not convenient if the mark is observed when the wearer is in public, and the common method of mark removal by rubbing with a dampened handkerchief is hindered by the hydrophobic nature of the structurant and carrier fluid.

Some manufacturers have proposed to add so called masking agents into cream formulations to reduce the visibility of the white marks, and to some extent this can be successful, especially for a period shortly after application of the formulation. However, it has now been observed that the effectiveness of masking agents can diminish with time, and this is particularly noticeable in respect of creams that contain aluminum/zirconium astringent salts and those which are structured using waxes. This can mean, for example, that a mark becomes more visible as the day progresses, if it is not removed quickly. Of course, it can be difficult to recognize immediately that a mark has occurred, when it exhibits only very low visible deposits initially. Visible deposits have been the subject of consumer complaints, not only to the brand owner, but the problem has also been raised on TV consumer programmes. Wax structurants are desirable in other ways; for example, they are readily available and formulations produced using them can have attractive sensory properties, but the problem of increased visibility of deposits during leave-on is one that remains.

Accordingly, it is an object of the present invention to devise wax-structured cream formulations that have a reduced tendency to exhibit visible marks during leave-on over an extended period of time.

SUMMARY OF THE INVENTION

According to the present invention there is provided an anhydrous antiperspirant cream composition comprising
 a) a particulate aluminum/zirconium astringent salt in an amount of from 5 to 30% by weight;
 b) a wax in an amount of from 4 to 20% by weight, said wax comprising an aliphatic ester or monohydric alcohol wax; and
 c) a water-immiscible carrier having a refractive index that is less than 0.1 below the refractive index of the aluminum/zirconium astringent salt and comprising an aromatic ester having a melting point of below 25° C. and/or a non-volatile silicone oil having a refractive index of at least 1.5 in an amount of from 45 to 80% by weight.

For an anhydrous antiperspirant cream composition herein, i.e. a soft solid, the hardness H will generally be from 0.003 to 0.5 N/mm$^2$, as measured by sphere indentation. Frequently, such hardness will be from 0.005 up to 0.1 N/mm$^2$.

Anhydrous herein indicates in the context of a cream composition that the composition does not comprise a liquid aqueous phase.

By formulating in accordance with the summary of the invention, it is possible to prepare anhydrous antiperspirant compositions in which an aluminum zirconium astringent salt suspended in a water-immiscible carrier fluid that is solidified by a wax exhibits improved resistance to the development of visible deposits over a period of time when exposed to the atmosphere after topical application. This accordingly ameliorates problems of white deposits appearing on the body or clothing several hours after contact with an antiperspirant formulation.

In a related second aspect of the present invention there is provided a process for preparing an anhydrous antiperspirant formulation in the form of a cream comprising the steps of:
 i) introducing into a mixing vessel a carrier fluid having a refractive index that is less than 0.1 below the refractive index of the aluminum/zirconium astringent salt and comprising an aromatic ester having a melting point of below 25° C. and/or a non-volatile silicone oil having a refractive index of at least 1.5 in an amount of from 50 to 80% by weight;

ii) introducing into the vessel a wax in an amount of from 4 to 20% by weight said wax comprising an aliphatic ester or monohydric alcohol wax;

iii) heating the non-polymeric wax until it melts or is miscible with the carrier fluid;

iv) introducing into the carrier fluid or mixture of carrier fluid and wax a particulate aluminum/zirconium astringent salt in an amount of from 5 to 30% by weight at a temperature above the normal solidification temperature of the formulation and;

v) introducing the composition into a dispenser whilst the composition is fluid.

In a further aspect of the present invention, there is provided a method for controlling or preventing perspiration by topically applying to the human body, and especially to the axilla a composition according to the first aspect described hereinabove.

DESCRIPTION OF PREFERRED EMBODIMENTS

The present invention relates to anhydrous cream formulations containing particulate antiperspirants in which the tendency for visible deposits to develop over time in wax-structured compositions is ameliorated or suppressed.

The antiperspirant active comprises suspended aluminum zirconium astringent salts.

Aluminum halohydrates employable herein are usually defined by the general formula $Al_2(OH)_xQ_y \cdot wH_2O$ in which Q represents chlorine, bromine or iodine, x is variable from 2 to 5 and x+y=6 while $wH_2O$ represents a variable amount of hydration. Preferably, the halohydrate is a chlorohydrate.

Zirconium salts for employment herein together with the aluminum salts can usually be represented by the empirical general formula: $ZrO(OH)_{2n-nz}B_z \cdot wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by $wH_2O$.

Preferably B represents chloride and the variable z lies in the range from 1.5 to 1.87. Zirconium aluminum chlorohydrate may be particularly preferred.

Antiperspirant complexes based on the above-mentioned astringent aluminum and/or zirconium salts can desirably be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$, for example the complexes with glycine as disclosed in U.S. Pat. No. 3,792,068 (Luedders et al). Certain of those Al/Zr complexes are commonly called ZAG in the literature. ZAG actives generally contain aluminum, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

The above aluminum and zirconium salts may have coordinated and/or bound water in various quantities and/or may be present as polymeric species, mixtures or complexes. Any bound or co-ordinated water therein is disregarded when determining whether or not the cream composition is anhydrous.

The particle size of the antiperspirant salts often falls within the range of 0.1 to 200 $\mu$m with a mean particle size often from 3 to 20 $\mu$m. Both larger and smaller mean particle sizes can also be contemplated such as from 20 to 50 $\mu$m or 0.1 to 3 $\mu$m. In it is also preferable to employ dense particulate materials, that is to say particulate antiperspirant salts that are not hollow. Hollow actives can be processed by milling to disintegrate the shell of the particle and thereby destroy the hollow.

The aluminum zirconium astringent salts tend to have a high refractive index. This is believed to contribute to the problem of visible deposits mentioned hereinbefore. Many of the preferred salts herein have a refractive index (at 25° C.) of 1.56±0.01. The instant inventors have found that it is desirable to control the difference in refractive index of the antiperspirant salt and the carrier fluid. Where the refractive index difference is too great, the resultant formulation can suffer from a tendency for visible deposits either to be too high from the outset, eg as demonstrated by a measurement on a product after 1 hour, and/or for the level of visible deposits to increase noticeably during leave-on over an extended period, eg as demonstrated by a measurement after 24 hours. According to the instant invention, the carrier fluid is chosen such that the difference in refractive index of the fluid and antiperspirant salt is less than 0.1.

In addition, the instant inventors have determined that the main or sole constituent of the carrier fluid should be selected from one of two classes of compounds, both of which are fluid under standard pressure at 25° C., the first class of which comprises aromatic esters and the second class of which comprises non-volatile silicone oils that have a refractive index of greater than 1.5. Within the first class, it is particularly desirable to select benzoate, naphthylate or salicylate esters. The esters desirably comprise the residue of one or more fatty alcohols, such as those containing from 10 to 22 carbons. A suitable example of such alcohol residues comprise alkyl mixtures containing from 12 to 15 carbons.

Amongst the class of benzoate esters, it is desirable to mention alkyl benzoate, alkylene dibenzoate, alkoxylated alkyl benzoate or a polyalkylene oxide dibenzoate, or a mixture of two or more sub-classes thereof. The alkyl group often contains at least 10 carbons, in many instances up to 25 carbons. It is often linear, but can alternatively be branched.

Especially desirable alkyl groups are found in the range of from 12 to 20 carbons and include dodecyl (lauryl) terdecyl, tetradecyl (myristyl), pentadecy, hexadecyl (palmityl), octadecyl (stearyl) 2-methyl-heptadecyl (iso-stearyl) and octyl-dodecyl groups. A mixture of two or more of the alkyl groups can be employed, such as a mixture of $C_{12}$–$C_{15}$ alkyl groups. The term alkylated herein includes alkylene groups and the latter are terminated at each end with a benzoate group. The alkylene group often contains from 2 to 6 carbons and can be linear or branched, a suitable example of linear being propylene.

In the alkoxylated alkyl benzoates contemplated herein, the alkyl group is terminated by an alkoxy group, which can be monomeric containing for example up to 6 carbons or polymeric such as polyethylene oxide or preferably polypropylene oxide, which conveniently comprises up to 30 units and often from 5 to 20 units. In such compounds, the alkyl group can be selected from the previously identified alkyl groups. Alternatively, the benzoate compound can comprise a polyethylene oxide or polypropylene oxide moiety, or preferably a block copolymer of ethylene oxide and propylene oxide, terminated at each end by a benzoate group. Mixtures of two or more of the benzoate sub-classes of compounds can be employed. Several preferred benzoate compounds are available from Finetex under their trade name Finsolv.

Suitable naphthylate and salicylate esters comprise alkylated naphthylate or salicylate, alkylated being as described above for benzoate esters.

Within the second class of carrier fluid, the silicone oils preferably comprise alkylaryl substituted polysiloxanes such as alkylphenyl substituted polysiloxanes, and especially methylphenyl polysiloxanes. Desirably, the polysiloxane is short chain and linear, such as a disiloxane, trisiloxane or tetrasiloxane. Particularly desirably, the mole ratio of alkyl (especially methyl) to phenyl substitution is 1:1. It is especially desirable to select within the class of non-volatile polysiloxane materials those which have a viscosity of below 300 centistokes and advantageously those of below 200 centistokes. In practice, the viscosity of preferred siloxane materials is often in the region of 50 centistokes or higher. The refractive index of preferred non-volatile silicone oils, such as those comprising alkylphenylsiloxanes normally is up to 1.56. Examples of highly preferred non-volatile siloxanes include PDM-7040 and PDM-7050 (trade names) obtainable from Gelest and DC 704 (trade name) obtainable from Dow Corning Inc.

In addition to the aforementioned classes of carrier fluid, it is possible to contemplate incorporating a minor fraction of a compatible co-carrier fluid. The proportion of any such co-carrier fluid is selected in conjunction with the carrier or mixture of carriers so as to enable the resultant mixture to have a refractive index of less than 0.1 below that of the antiperspirant salt. The RI of the mixture can be calculated by determining the weighted average of individual constituents of the mixture $$RI_{mix} = \Sigma(RI_n \cdot w_n)/\Sigma(w_n)$$

where $RI_n$ is the refractive index of a constituent n and $RI_{mix}$ that of the mixture, and $w_n$ is the weight of that constituent.

Amongst the co-carriers that can be contemplated, readily available co-carriers comprise volatile silicones, volatile hydrocarbon oils and non-volatile hydrocarbon oils. Volatile silicones are those silicone oils that have a measurable vapour pressure at 20 or 25° C. Typically the vapour pressure of a volatile silicone lies in a range from 1 or 10 Pa to 2 kPa at 25° C. The volatile silicones commonly comprise either dimethicones or cyclomethicones containing from 4, 5 or 6 silicone units, having a molecular weight in the range of 220 to 380.

Many suitable volatile hydrocarbon oils comprise branched chain isoparaffins of intermediate chain length, conveniently from 6 to 25 carbons, such as Isopar™ C, E, G H or L. Other examples of such hydrocarbons include Permethyl™ 99A, 101A and 102A. Linear hydrocarbon oils include octane, decane and dodecane. Non-volatile hydrocarbon oils often contain from 20 to 40 carbons on average and include mineral oil and hydrogenated polydecene, for example those sold under the trademark SilkFlo™ 364.

Preferably, the proportion of such co-carrier(s) in the formulation comprises not more than 15% in total. It is particularly suitable to incorporate the co-carrier(s) in a ratio to the carrier(s) of not more than 1:3 and especially not more than 1:4. By restricting the proportion of co-carrier in the formulation, it is possible to avoid formulations having a milky appearance on topical application if too much volatile silicone is present and of impairing the sensory properties of the formulation if too much non-volatile hydrocarbon is employed.

The invention compositors employ from 4 to 20% by weight of wax, and in many embodiments from 5 to 15% by weight. In some preferred compositions, the wax content is from 8 to 12% by weight.

Incorporation of a wax or mixture of waxes structures the carrier fluids and when present any co-carrier fluids. Herein, the term "wax" is as conventionally applied to a variety of materials and mixtures that have similar physical properties, namely that:

they are solid at 30° C. and preferably also at 40° C.; they melt to a mobile liquid at a temperature above 30° C. but generally below 95° C. and preferably in a temperature range of 40° C. to 90° C.;

they are water-insoluble and remain water-immiscible when heated above their melting point; they form crystals in the water-immiscible liquid when it cools from the heated state during processing.

The present invention employs one or more waxes comprising aliphatic monohydric alcohols, otherwise often called fatty alcohols, and preferably aliphatic esters containing the residue of a fatty acid or fatty alcohol or a mixture of such compounds. Such waxes may be synthetic or naturally occurring, or obtainable by processing of naturally occurring products, such as by hydrogenating unsaturated oils. Naturally occurring waxes or waxes derived from naturally occurring oils are often mixtures of compounds which include a substantial proportion, likely to be a majority, of fatty esters.

Examples of ester waxes include esters in the range of $C_{16}$ to $C_{40}$ fatty acids with glycerol or ethylene glycol and these may be made synthetically. The esters include for example glyceryl di or tri-esters and glycol diesters. Commonly, the ester component of glycol or glyceryl waxes are derived from selected narrower ranges of fatty acids, such as from $C_{16}$ to $C_{22}$ or $C_{24}$, predominantly $C_{18}$, or $C_{20}$ to $C_{36}$ or $C_{40}$. Alternatively the product can comprise glyceryl or glycol esters derived from natural products, such as hydrogenated castor oil, often referred to as castor wax. The ester waxes or significant individual components of ester wax mixtures include glyceryl palmitate, glyceryl stearate, glyceryl behenate, glycol stearate and glycol behenate. A number of suitable ester waxes are sold by Croda under their trade mark Syncrowax, such as grades BB-4, HGL-C, ERL-C, HR-C, and HRS-C or by Koster Keunen under their mark Kesterwax, sometimes abbreviated to K, as in K62, K69, K72, K82 and K85.

Examples of natural waxes include beeswax, spermaceti, baysberry, carnauba and candellila waxes that are of vegetable origin and mineral waxes from fossil remains other than petroleum. Montan wax, which is an example of mineral wax, includes non-glyceride esters of carboxylic acids, hydrocarbons and other constituents.

The ester waxes or natural waxes containing ester compounds can constitute all of the wax, if desired, and preferably constitutes at least 70% and especially at least 80% by weight of the total weight of waxes.

The other waxes contemplated herein as an alternative to or together with the fatty esters are linear aliphatic fatty alcohols, such as those containing from 16 to 24 carbon atoms, such as cetyl alcohol, stearyl alcohol and behenyl alcohol. However, such materials tend to create visible deposits to a greater degree than do the ester waxes, so that it is preferable to employ either no linear fatty alcohols, or substantially none, by which is meant not more than 1% and preferably less than 0.5% of the composition. Expressed differently, linear fatty alcohols more preferably constitute no more than 5% of the total weight of the composition.

In addition to the foregoing classes of waxes, and particularly the ester waxes, other waxes can be contemplated. Such supplementary waxes can be chosen from hydrocarbon waxes, and silicone waxes. The supplementary waxes often contribute from 0 to 7% of the wax blend.

Examples of hydrocarbon waxes include paraffin wax, Fischer-Tropsch waxes and microcrystalline wax.

Examples of silicone waxes employable herein commonly comprise silicone polymer waxes, such as those which satisfy the empirical formula:

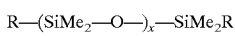

$$R\text{—}(SiMe_2\text{—}O\text{—})_x\text{—}SiMe_2R$$

in which x is at least 10, preferably 10 to 50 and R represents an alkyl group containing at least 20 carbons, preferably 25 to 40 carbons, and particularly having an average linear chain length of at least 30 carbons.

Other suitable silicone waxes comprise copolymers of dimethicone and alkyloxymethicone, satisfying the general formula:

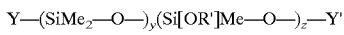

$$Y\text{—}(SiMe_2\text{—}O\text{—})_y(Si[OR']Me\text{—}O\text{—})_z\text{—}Y'$$

in which Y represents $SiMe_2$—O, Y' $SiMe_2$, R' an alkyl of at least 15 carbons preferably 18 to 22 such as stearyl, y and z are both integers, totaling preferably from 10 to 50.

Waxes useful in the present invention will generally be those found to thicken water-immiscible oils such as cyclomethicones when dissolved therein (by heating and cooling) at a concentration of 5 to 15% by weight.

Although single waxes may be employed herein, it is often preferable to employ a combination of waxes, differing for example by their chemical constitution and/or their melting point. Thus, one suitable combination comprises a mixture of a higher melting point wax, i.e. one having a melting point of at least 75° C., often not higher than 85° C., with a lower melting point wax, i.e. one which melts at a lower temperature of below 75° C., though many examples melt at above 60° C. The weight ratio of higher to lower melting point wax is often chosen in the range of from 2:1 to 4:1. One suitable example of a mixture of different waxes comprises castor wax with a glycol or glycerol ester, for example that sold under the trade mark/grade Syncrowax ERL-C.

In practice, the proportion of wax in the mixture is often selected in the range of from 6% to 15%, and in many embodiments from 7.5% to 12.5%. The weight ratio of carrier fluid and any co-carrier fluid to wax is in many formulations selected in the range of from 4:1 to 10:1 and particularly from 5:1 to 8:1.

If desired, the wax can be supplemented by incorporating a particulate thickening agent, such a particulate silica or clay, such as in an amount of up to about 2% by weight. A suitable silica comprises fumed silica such as those available from Degussa under their mark Aerosil and a suitable clay is often a hectorite or bentonite such as that available from Rheos under their mark Bentone. In copending PCT application no PCT/EP 01/00186, cream compositions are described which contain thickening polymers. The compositions of the instant invention can be obtained without the incorporation of and are preferably free from such thickening polymers.

Other Constituents

Optional ingredients in compositions of this invention can include deodorants, for example at a concentration of up to about 10% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as triclosan (Irgasan DP300™), chlorhexidine and Tricloban™, warrant specific mention. A yet another class comprises biguanide salts such as available under the trade mark Cosmosil™.

A yet further class of antimicrobial which can advantageously be employed herein comprises transition metal chelators, such as amino acids or salts thereof, which chelators have affinity for iron (III), and preferably a binding constant for iron (III) of greater than $10^{10}$, or, for optimum performance, greater than $10^{26}$. The 'iron (III) binding constant' referred to above is the absolute stability constant for the chelator-iron (III) complex. One especially preferred chelator is DTPA (diethylene triamine pentaacetic acid) and salts thereof. Such antimicrobials suppress microbial regrowth. A convenient amount is from 0.35 to 2% by weight.

In practice, an optional though highly desirable component comprises a wash-off aid, preferably at a concentration of from at least 0.2% to 10% by weight and particularly from 0.5% to 5% by weight of the formulation. It assists the removal of the formulation from the skin to control build-up on the skin. The wash-off aid is and particularly at least 1%, such as up to 5% w/w of the formulation. Expressed in alternative fashion, the wash-off aid is desirably present in a weight ratio to the water-immiscible oil of from 1:10 to !:100, and especially from 1:5 to 1:40 w/w. The wash off aid is commonly a non-ionic surfactant, often having an HLB value of from about 6 to about 15, and especially is a polyalkylene oxide (eg PEO or PEO/PPO) ether or ester derivative of a fatty alcohol or acid, possibly including an intermediary polyhydric alcohol residue, eg from glycerol. Examples include seteth-15, steareth-25 and ceteareth-20.

Other optional ingredients can be incorporated to the extent that they are miscible with the carrier fluids. They include skin benefit agents such as glycerol, and allantoin or lipids, for example in an amount of up to 5%; oil-soluble colorants; skin cooling agents such as menthol and menthol derivatives, often in an amount of up to 2%, all of these percentages being by weight of the formulation. A commonly employed and highly desired ingredient is a perfume, which is normally present at a concentration of from 0 to 4% and in many formulations from 0.25 to 2% by weight thereof.

The formulations described herein can be produced by any method that has been described previously for preparing an anhydrous soft solid formulation in which a particulate antiperspirant active is suspended in a water-immiscible oil that is structured into a solid mass by incorporation of a wax or mixture of waxes.

In general, the preparative process comprises introducing the wax or mixture of waxes into the water-immiscible oil or blend of oils and both heating and agitating the resultant mass until the waxes dissolve in the oil forming an homogenous blend. The waxes can be pre-melted if desired. The oil/wax mass is preferably heated to above the melting point of the wax having the highest melting point. In many instances, this is a temperature in the region of from 75 or 80° C. to 90° C.

In a separate step, the antiperspirant actives are introduced into the formulation. Although this can be before the mass of oil and wax is heated, it occurs preferably after the mass has been homogenised, and in many instances can occur after the mass has cooled somewhat. A temperature range of below 70° C. has been recommended, but a temperature of over 70° C. is often acceptable. The further ingredients of the formulation are introduced at a time of convenience to the producer. Thus, for example, it can be particularly convenient to introduce particulate materials together with the antiperspirant active, and wash-off aids into the oil together with the wax. Any temperature sensitive ingredients, of which perfume can be one, are most preferably added last and at the lowest temperature.

When the formulation has been produced in a fluid form, it is then packaged. This is the commonly achieved by introducing the fluid material into a dispensing container, at a temperature which is a little higher than the normal setting temperature of the formulation, such as from 5 to 10° C. above, which is thereafter cooled or allowed to cool to below the solidification temperature. The setting temperature is commonly is at least about 50° C. for wax-structured formulations. In order to encourage the formulation to adopt a soft solid form rather than a firm solid form, it is possible to continue subjecting the formulation to high shear mixing during cooling at or through the temperature at which the formulation would normally solidify, i.e. in the absence of shearing and which had previously been determined. Alternatively, fluidity can be attained by injecting the composition under pressure into the dispenser.

The formulations herein are capable of being dispensed using soft solid dispensers such as those described in U.S. Pat. No. 5,000,356, U.S. Pat. No. 5,639,622, U.S. Pat. No. 5,725,133, or U.S. Pat. No. 6,039,483. The dispenser commonly contains from 10 to 100 g formulation. The invention formulations can be applied to skin in the conventional manner by extruding a desired amount of formulation on to the contact surface of the head of the dispensing container, normally through one or more apertures in the head, and thereafter wiping the head across the surface of the skin, and particularly in the axilla. Having given a detailed description of and preferences for the invention above, certain embodiments thereof will now be described more fully by way of example.

The ingredients employed in the Examples were as follows:

| Ingredient | Tradename/Supplier |
| --- | --- |
| $C_{18-36}$ glycol esters | Syncrowax ERL-C, Croda |
| Glycerol tribehenate | Syncrowax HRC, Croda |
| $C_{18-36}$ glycerol | Syncrowax HGL-C, Croda |
| Hydrogenated caster oil | Castorwax MP80, CasChem |
| stearoxymethicone/ dimethicone copolymer | Masilwax 135, BASF |
| Arachidyl Behenate | Waxenol 822, Paroxite |
| Behenyl Alcohol | Stenol 1822, Cognis |
| Silica | Aerosil 200, Degussa |
| $C_{12-15}$ alkyl benzoate [RI 1.4841] | Finsolv TN, Finetex |
| Isostearyl benzene [RI 1.4860] | Finsolv SB, Finetex |
| $C_{12-15}$ alkyl benzoate/ dipropylene glycol dibenzoate/ PPG15 stearyl ether benzoate [RI 1.4915] | Finsolv TPP, Finetex |
| Diethylhexyl 2,6-naphthalate [RI 1.5320] | HallBrite TQ, C. P Hall |
| Butyloctyl salicylate [RI 1.4912] | HallBrite BHB, C. P Hall |
| tetramethyl tetraphenyl trisiloxane [RI 1.5620] | DC704, Dow Corning |
| cyclomethicone [RI 1.3997] | DC245, Dow Corning |
| Hydrogenated Polydecene [RI 1.4544] | Silkflo 364NF, Albemarle |
| Al/Zr tetrachlorohydrex glycine complex (AZAG) | Q5 7167, Summit |
| Al/Zr tetrachlorohydrex glycine complex (AZAG) | Reach 908, Reheis |

EXAMPLES 1 AND 2

In these Examples, formulations as described in Table 1 below were prepared by heating and agitating a mixture of the waxes and carrier fluid to a temperature of about 80° C. to form a homogenous mixture, allowing the mixture to cool to between 70 and 75° C. whilst maintaining agitation, introducing the particulate antiperspirant active and any other particulates, cooling and shear mixing the resultant mixture until a temperature of from 55 to 60° C. was attained and then pouring the mixture into soft solid dispensers according to U.S. Pat. No. 6,039,483. The formulations obtained were opaque soft solids.

The hardness and visible deposits of the Example formulations were measured in the manner described below and the results summarised in Table 1.

TABLE 1

|  | % by weight | |
| --- | --- | --- |
|  | Ex1 | Ex2 |
| Ingredients | | |
| Syncrowax ERL-C | 2.5 | 2.5 |
| Castorwax MP80 | 7.5 | 7.5 |
| Aerosil 200 |  | 0.5 |
| Finsolv TN | 63.5 |  |
| Finsolv SB |  | 63 |
| AZAG Q5 7167 | 26.5 | 26.5 |
| Properties | | |
| Hardness (N/mm$^2$) | 0.031 | 0.092 |
| Visible Deposits (1 hr) | 8 | 9 |
| Visible Deposits (24 hr) | 9 | 12 |

From Table 1, it can be seen that the formulations not only enjoyed very low visible deposits initially, as demonstrated by the data at 1 hour, but also that the deposits increased to only a very limited extent during leave-on over time, as demonstrated by the data at 24 hours, the level of visible deposits remaining within the qualitative description of very low.

By way of comparison, similar measurement of visible deposits were made on a commercially available soft solid that employs a predominantly volatile silicone carrier fluid structured using a mixture of glyceride ester waxes, using the same equipment and methodology. Although the commercial formulation initially exhibited very low visible deposits of 11 after 1 hour, the extent of visible deposits increased markedly with the passage of time, recording 36 after 24 hours. Thus, although material from the commercial product that transferred onto clothing initially had a relatively low risk of being observed, as time passed, it became increasingly visible.

EXAMPLES 3 TO 8

These Examples were made by the following general process, except that in Example 4, the non-AP active components were heated to 80° C. at which temperature the antiperspirant active was added and in Example 8, the non-AP active components were heated to 85° C.

In the general process, conducted on a 100 g scale in a tall beaker (250 mls) equipped with a L4RT Silverson, 1 inch head with square mesh, high shear screen, all the ingredients summarised in Table 2 below, with the exception of the antiperspirant active were introduced into the beaker, stirred and heated to 90° C. The mixture was allowed to cool to 85° C. whereupon the antiperspirant active (ambient temperature of about 22° C.) was introduced with stirring in a single batch, cooling the formulation by about 20° C. The formulation was stirred for one minute at about 10000 rpm and thereafter allowed to cool with occasional stirring with a spatula until it attained the temperature specified in Table 2 below, at which it was poured into soft solid dispensers as described in U.S. Pat. No. 6,039,483. The hardness and visible deposits were measured in the same way as for Examples 1 and 2 and the results summarised in Table 2 below.

TABLE 2

| | % by weight | | | | | |
|---|---|---|---|---|---|---|
| | 3 | 4 | 5 | 6 | 7 | 8 |
| Ingredient | | | | | | |
| Syncrowax ERL-C | 2.5 | | | | | |
| Syncrowax HRC | | | | 6 | | |
| Syncrowax HGL-C | | | | | 1.5 | |
| Castorwax MP80 | 7.5 | 7.5 | 7.5 | 7.5 | | 7.5 |
| Masilwax 135 | | 2.5 | | | | 2.5 |
| Waxenol 822 | | | 2.5 | | | |
| Stenol 1822 | | | | 2.5 | | |
| Silica | | | 0.5 | | | |
| Finsolv TN | 32 | | 53.5 | 59 | 56.5 | |
| Finsolv TPP | | 54 | | | | 54 |
| HallBrite TQ | | 10 | | | | |
| HallBrite BHB | | | | | | 10 |
| DC704 | 32 | | | | | |
| DC245 | | | 10.0 | | 10.0 | |
| Silkflo 364NF | | | | 5 | | |
| Reach 908 | 26 | 26 | 26 | 26 | 26 | 26 |
| Properties | | | | | | |
| Pour temperature (° C.) | 557 | 56 | 62 | 65 | 61 | 65 |
| Hardness (N/mm²) | 0.053 | 0.029 | 0.037 | 0.053 | 0.009 | 0.007 |
| Visible Deposits (1 hr) | 12 | 11 | 10 | 11 | 11 | 9 |
| Visible Deposits (24 hrs) | 12 | 11 | 10 | 12 | 11 | 10 |

From Table 2, it can be seen that the further Examples of soft solid formulations demonstrated not only a very low visible deposit when applied, as shown by the measurement after 1 hour, but that such visibility of deposits remained very low during longer than the normal period of leave on (i.e. before it is washed off) as shown by the measurement after 24 hours.

Measurement of Properties i) Hardness

Texture Analyser

This test apparatus can move a blunt probe into or out from a sample at a controlled speed and at the same time measure the applied force. The parameter which is determined as hardness is a function of the force and the projected area of indentation.

A specific test protocol used a Stable Micro systems TA.XT2I™ Texture Analyser. A sample of composition was made by heating the ingredients, pouring into a container and allowing to cool as described above. The container was a 15 ml glass jar with a wide mouth. A metal sphere, of diameter 9.5 mm, was attached to the underside of the Texture Analyser's 5 kg load cell such that it could be used for indenting a sample placed beneath it on the base plate of the instrument. After positioning the sample, the sphere position was adjusted until it was just above the sample surface. Texture Expert Exceed™ software was used to generate the subsequent motion profile used in the test method. This profile initially moved the sphere into contact with the sample and then indented the sphere into the sample at an indentation speed of 0.05 mm/s for a distance of 7 mm. At this distance the direction of motion of the sphere was immediately reversed to withdraw the sphere from the sample at the same speed of 0.05 mm/s. During the course of the test, the data acquired were time(s), distance (mm) and force (N) and the data acquisition rate was 25 Hz.

The data associated with each test were manipulated using standard spreadsheet software and used to calculate the hardness, H, at a travelled distance of 4.76 mm after initial contact with the sample, using the following equation:

$$H = F/A$$

(H expressed in $N.mm^{-2}$, F in N and A in $mm^{-2}$)

where F is the load at the same travelled distance and A is the projected area of the indentation. This area can be calculated geometrically and is equal to the area of a diametral plane of the sphere, i.e. $\pi \times (4.76)^2$ $mm^2$.

ii) Whiteness of Deposit

Another test of the properties of a composition is the whiteness and hence opacity of the composition which is delivered onto a surface when the composition is drawn across that surface (representing the application of the composition to human skin). To carry out this test of deposition, a sample of the composition was first applied to a test fabric under standardised conditions.

The test fabric was a rectangular strip of black worsted wool fabric 9 cm by 15 cm. This was placed in an apparatus consisting of a metallic base onto which was hinged a metallic frame defining a rectangular aperture of 5 cm by 9 cm. The test portion of fabric was laid on the base. The hinged frame was placed over the fabric and secured to the base by means of two screws thereby clamping the test fabric in place but exposing an area of 5×9 cm through the aperture.

A sample of soft solid composition in a dispensing container was kept at ambient laboratory temperature (about 20° C.) before it was required for measurement. A portion of the composition is then extruded from the container through the dispensing apertures at one end. A weight amount (0.5 g) of the extruded composition was spread uniformly across the 5×9 cm area of test fabric enclosed by the frame. Spreading was carried out using a plastic spreading tool. After spreading the sample of composition on the fabric substrate, it was removed from the apparatus and weighed to check that the mass of applied sample was 0.5±0.01 g.

The fabric with applied sample of composition was then assessed twice for whiteness, once after one hour and again after 24 hours.

This measurement was carried out using a Sony XC77™ monochrome video camera with a Cosmicar™ 16 mm focal length lens positioned vertically above a black table illuminated from a high angle using fluorescent tubes to remove shadowing. The apparatus was initially calibrated using a reference white card, after the fluorescent tubes had been turned on for long enough to give a steady light output. The cloth with a deposit thereon was placed on the table and the camera was used to capture an image. An area of the image of the deposit was selected and analysed using a Kontron IBAS™ image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen. All samples were prepared in triplicate and a mean of the three measured values was reported.

We claim:

1. An anhydrous antiperspirant cream composition comprising
   a) a particulate aluminum/zirconium astringent salt in an amount of from 5 to 30% by weight;
   b) a wax in an amount of from 4 to 20% by weight comprising an aliphatic ester or monohydric alcohol wax; and
   c) a water-immiscible carrier having a refractive index that is less than 0.1 below the refractive index of the aluminum/zirconium astringent salt and comprising an aromatic ester having a melting point of below 25° C. and/or a non-volatile silicone oil having a refractive index of at least 1.5 in an amount of from 45 to 80% by weight.

2. A composition according to claim 1 in which the wax comprises less than 1% by weight of a linear fatty alcohol.

3. A composition according to claim 1 in which the non-polymeric wax is a mixture of ester waxes.

4. A composition according to claim 1 in which the carrier fluid comprises an alkyl benzoate.

5. A composition according to claim 1 in which the carrier fluid is employed in conjunction with a co-carrier fluid which constitutes not more than 15% by weight of the composition.

6. A composition according to claim 5 in which the carrier fluid comprises an alkyl benzoate.

7. A composition according to claim 5 in which the co-carrier fluid comprises a volatile silicone or a volatile or non-volatile hydrocarbon oil.

8. A composition according to claim 1 which additionally contains up to 2% by weight of an inorganic particulate thickener.

9. A composition according to claim 8 in which the thickener comprises a fumed silica.

10. A composition according to claim 1 which is free from a thickening polymer.

11. A process for making an anhydrous soft solid antiperspirant formulation in the form of a cream comprising the steps of:
    i) introducing into a mixing vessel a carrier fluid having a refractive index that is less than 0.1 below the refractive index of an aluminum/zirconium astringent salt and comprising an aromatic ester having a melting point of below 25° C. and/or a non-volatile silicone oil having a refractive index of at least 1.5 in an amount of from 50 to 80% by weight;
    ii) introducing into the vessel a wax in an amount of from 4 to 20% by weight comprising an aliphatic ester or monohydric alcohol wax;
    iii) heating the non-polymeric wax until it melts or is miscible with the carrier fluid;
    iv) introducing into the carrier fluid or mixture of carrier fluid and wax a particulate aluminum/zirconium astringent salt in an amount of from 5 to 30% by weight at a temperature above the normal solidification temperature of the formulation and;
    v) introducing the composition into a dispenser whilst the composition is fluid.

12. A cosmetic method for controlling or preventing perspiration by topically applying to the human body, and especially to the axilla a composition according to claim 1.

* * * * *